(12) United States Patent
Benezra et al.

(10) Patent No.: US 9,393,317 B2
(45) Date of Patent: Jul. 19, 2016

(54) PEPTIDE-CONJUGATED OLIGONUCLEOTIDE THERAPEUTIC AND METHOD OF MAKING AND USING SAME

(71) Applicant: Sloan-Kettering Institute for Cancer Research, New York, NY (US)

(72) Inventors: Robert Benezra, New York, NY (US); Erik Henke, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 14/551,641

(22) Filed: Nov. 24, 2014

(65) Prior Publication Data

US 2015/0087599 A1 Mar. 26, 2015

Related U.S. Application Data

(60) Division of application No. 12/829,783, filed on Jul. 2, 2010, now Pat. No. 8,895,701, which is a continuation-in-part of application No. PCT/US2009/030164, filed on Jan. 5, 2009.

(60) Provisional application No. 61/019,244, filed on Jan. 5, 2008, provisional application No. 61/027,100, filed on Feb. 8, 2008, provisional application No. 61/222,633, filed on Jul. 2, 2009.

(51) Int. Cl.
| | |
|---|---|
| *A61K 38/00* | (2006.01) |
| *C07K 16/00* | (2006.01) |
| *A61K 47/48* | (2006.01) |
| *C07K 7/06* | (2006.01) |
| *C07K 7/08* | (2006.01) |
| *C07K 14/00* | (2006.01) |
| *C12N 15/113* | (2010.01) |
| *A61K 31/713* | (2006.01) |
| *A61K 45/06* | (2006.01) |

(52) U.S. Cl.
CPC ......... *A61K 47/48246* (2013.01); *A61K 31/713* (2013.01); *A61K 45/06* (2013.01); *A61K 47/48092* (2013.01); *C07K 7/06* (2013.01); *C07K 7/08* (2013.01); *C07K 14/001* (2013.01); *C12N 15/113* (2013.01); *A61K 38/00* (2013.01); *C12N 2310/11* (2013.01); *C12N 2310/315* (2013.01); *C12N 2310/321* (2013.01); *C12N 2310/341* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,391,723 | A | 2/1995 | Priest |
| 5,670,617 | A | 9/1997 | Frankel et al. |
| 6,372,433 | B1 | 4/2002 | Baker et al. |
| 2002/0041898 | A1 | 4/2002 | Unger et al. |
| 2003/0109550 | A1 | 6/2003 | Clare et al. |
| 2003/0149235 | A1 | 8/2003 | Baker et al. |
| 2003/0152578 | A1 | 8/2003 | Ruoslahti et al. |
| 2004/0072191 | A1 | 4/2004 | Chenchik |
| 2004/0077574 | A1 | 4/2004 | Klinghoffer et al. |
| 2004/0102458 | A1 | 5/2004 | Chiosis et al. |
| 2004/0127450 | A1 | 7/2004 | Narayanan |
| 2005/0032726 | A1 | 2/2005 | Li et al. |
| 2005/0042646 | A1 | 2/2005 | Davidson et al. |
| 2005/0049263 | A1 | 3/2005 | Kasibhatla et al. |
| 2005/0107343 | A1 | 5/2005 | Kasibhatla et al. |
| 2005/0113339 | A1 | 5/2005 | Kasibhatla et al. |
| 2005/0124569 | A1 | 6/2005 | Guerciolini et al. |
| 2005/0137155 | A1 | 6/2005 | McSwiggen et al. |
| 2005/0171039 | A1 | 8/2005 | McSwiggen et al. |
| 2005/0196767 | A1 | 9/2005 | McSwiggen et al. |
| 2005/0209179 | A1 | 9/2005 | McSwiggen et al. |
| 2006/0094676 | A1 | 5/2006 | Lahav et al. |
| 2006/0205705 | A1 | 9/2006 | Ross et al. |
| 2006/0252037 | A1 | 11/2006 | Kolesnick et al. |
| 2007/0072855 | A1 | 3/2007 | Barrilalonso et al. |

FOREIGN PATENT DOCUMENTS

| | | | |
|---|---|---|---|
| EP | 1797901 | * | 12/2005 |
| EP | 1797901 | A1 | 6/2007 |
| WO | 9606641 | | 3/1996 |
| WO | 2005089106 | A2 | 9/2005 |

OTHER PUBLICATIONS

Merck Manual Colorectal Cancer accessed Aug. 21, 2014 at URL merckmanuals.com/home/digestive_disorders/tumors_of_the_digestive_system/colorectal_cancer.html).*
Overview of Leukemia at URL merckmanuals.com/home/blood_disorders/leukemias/overview_of_leukemia.html?qt=Leukemia&alt=sh accessed Aug. 20, 2014).*
National Institute of Cancer—understanding and related topics, accessed Aug. 21, 2014 at URL: cancer.gov/cancertopics/understandingcancer.*

(Continued)

*Primary Examiner* — Jeanette Lieb
(74) *Attorney, Agent, or Firm* — Larson & Anderson, LLC

(57) ABSTRACT

Conjugates for the efficient delivery of sequence-specific antisense to cells of a selected type for the inhibition of a target protein have the general formula:

peptide-HBL-antisense in which the peptide is a homing peptide which directs the conjugate to cells of a particular type, antisense is an antisense oligonucleotide having a sequence selected to provide sequence-specific inhibition of the target protein, and HBL is a heterobifunctional linker having reactivity towards amino and sulfhydryl groups.

23 Claims, 6 Drawing Sheets

(56) References Cited

OTHER PUBLICATIONS

Merck Manuals Brain Tumors accessed Aug. 21, 2014 at URL merckmanuals.com/home/brain_spinal_cord_and_nerve_disorders/tumors_of_the_nervous_system/brain_tumors.html).*
Merck Manual Breast Cancer accessed Aug. 21, 2014 at URL: merckmanuals.com/home/womens_health_issues/breast_disorders/breast_cancer.html).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh.*
Ovarian Cancer, accessed Aug. 21, 2014 at merckmanuals.com/home/womens_health_issues/cancers_of_the_female_reproductive_system/ovarian_cancer.html?qt=ovarian cancer&alt=sh.*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html.*
Merck Manual Cancer of the Uterus, accessed Aug. 21, 2014 at URL: merckmanuals.com/home/womens_health_issues/cancers_of_the_female_reproductive_system/cancer_of_the_uterus.html?qt=Cancer of the Uterus&alt=sh.*
Moulton, Bioconjugate Chem., vol. 15, No. 2, 2004.*
Arap, Marco A et al. "Cell Surface expression of the stress response chaperone GRP78 enables tumor targeting by circulating ligands" Sep. 2004, pp. 275-284, vol. 6, Cell Press.
Auerbach, Robert et al. "Angiogenesis Assays: A Critical Overview", 2003, pp. 32-40, vol. 49, No. 1, Clinical Chemistry.
Carmeliet, Peter et al. "Angiogenesis in cancer and other diseases", 2000, pp. 249-257, vol. 407, Nature.
Chaudhary, Jaideep et al. "Hoormonal Regulation and Differential Action of the Helix-Loop-Helix Transcriptional Inhibitors of Differentiation (Id1, Id2, Id3, and Id4) in Sertoli Cells", 2001, pp. 1727-1736, vol. 142, No. 5, The Endocrine Therapy.
de Candia, Paola et al. "Angiogenesis impairment in Id-deficient mice cooperates with an Hsp90 inhibitor to completely suppress HER2/neu-dependent breast tumors", Oct. 2003, pp. 12337-12342, vol. 100, No. 21, PNAS.
Dmitri, A et al. "Expression and Distribution of id helix-loop-helix protein in human astrocytic tumors", 2002, pp. 329-338, vol. 38, Issue 4, GLIA, Abstract Only.
Fu, Hui et al. "Dual origin of spinal oligodendrocyte progenitors and evidence for the cooperative role of Olig2 and Nkx2.2 in the controll of oligodendrocyte differentiation" 2002, pp. 681-693, vol. 129, Development.
Harrison, Joseph et al. "Synthesis and hybridization analysis of a small library of peptide-oligonucleotide conjugates", 1998, vol. 26, No. 13, Nucleic Acids Research.
Kleeff, Jorg et al. "The Helix-Loop-Helix Protein Id2 is Overexpressed in Human Pancreatic Cancer", 1998, pp. 3769-3772, vol. 58, Cancer Research.
Lee, Tong-Young et al. "Peptide-Mediated Targeting to Tumor Blood Vessels of Lung Cancer for Drug Delivery" 2007, pp. 10958-10965, vol. 67, No. 22, Cancer Research.
Ligon, Keith et al. "Olig2-regulated lineage-restricted pathway controls replication competence in neural stem cells and malignant glioma" 2007, pp. 503-517, vol. 53, No. 4, NIH Public Access.
Oku, Naoto et al. "Anti-neovascular therapy using novel peptides homing to angiogenic vessels", 2002, pp. 2662-2669, vol. 21, Oncogene.
Porkka, Kimmo et al. "A fragment of the HMGN2 protein homes to the nuclei of tumor cells and tumor endothelial cells in vivo" May 2002, pp. 7444-7449, vol. 99, No. 11, PNAS.
Rubenstein, Marvin et al. "Construction of a bispecific antisense oligonucleotide containing multiple binding sites for the treatment of hormone insensitive prostate tumors" 2005, pp. 905-907, vol. 65.
Seaman, Steven et al. "Genes that Distinguish Physiological and Pathological Angiogenesis", Jun. 2007, pp. 539-554, vol. 11, Cancer Cell.
St. Croix, Brad et al. "Genes Expressed in Human Tumor Endothelium" Aug. 2000, pp. 1197-1202, vol. 289, Science.
Weiss, B et al. "Antisense RNA gene therapy for studying and modulating biological processes", 1999, pp. 334-358, vol. 55, Cell. Mol. Life Sci.
Krumpe, L et al. "The use of Phage-Displayed Peptide Libraries to Develop Tumor-Targeted Drugs" International Journal of Peptide Research and Therapeutics, Mar. 2006, pp. 79-91, vol. 12 No. 1.
Shadidi, M. et al. "Selective Targeting of Cancer Cells using Synthetic Peptides" Drug Resistance Updates, 2003, pp. 363-371, vol. 6.
Harrison and Balasubramanian "Synthesis and hybridization analysis of a small library of peptide-oligonucleotide conjugates" Nucleic Acid Research, 1998, pp. 3136-3145, vol. 26, No. 13.
Tung, C.H. et al. "Tat Peptide-oligonucleotide conjugates" Bioconjugate chem., 1995, pp. 292-295, vol. 6.
Juliano, R.L. "Intracellular Delivery of Oligonucleotide Conjugates and Dendrimer Complexes" Ann. N.Y. Acad. Sci. 2006, pp. 18-26, vol. 1082.
Moulton, H. et al. "Cellular Uptake of Antisense Morpholino Oligomers Conjugated yo Arginine-Rich Peptides" Bioconjugate Chem. 2004, pp. 290-299, vol. 15.

* cited by examiner

PEPTIDE-CONJUGATED OLIGONUCLEOTIDE THERAPEUTIC AND METHOD OF MAKING AND USING SAME

RELATED APPLICATIONS

This application is a continuation-in-part of PCT Application No. PCT/US09/30164, filed Jan. 5, 2009, which claims priority from U.S. Provisional Application 61/019,244 filed Jan. 5, 2008 and 61/027,100 filed Feb. 8, 2008, all of which are incorporated herein by reference.

The application also claims the benefit of U.S. Provisional Application No. 61/222,633, filed Jul. 2, 2009, which application is incorporated herein by reference.

BACKGROUND OF THE INVENTION

This application relates to a peptide-conjugated oligonucleotide therapeutic agent and to methods of using same in therapy.

Sequence-specific antisense oligonucleotides are well known both as a concept for providing targeted therapy, and as myriad specific agents directed to specific targets. Sequence-specific antisense oligonucleotides interact with mRNA having a complementary sequence to interfere with expression of the protein encoded by the mRNA. Crooke, S. T. "Basic Principles of Antisense Therapeutics" in *Antisense Research and Application*, Pages 1-52, Springer (1998). Because the sequence of the antisense can be selected to complement the mRNA for just one protein, sequence-specific antisense oligonucleotides have been seen as offering vast potential for the treatment of many types of disease characterized by protein over-expression. To date, however, this potential has not been realized, owing in part to the inability to reliably deliver effective amounts of the oligonucleotide into the cells containing the target mRNA in vivo.

Various strategies have been proposed to overcome these difficulties so that antisense therapy can realize its potential. In some proposals, vectors are introduced which lead to the in situ production of antisense species (either full length or as oligonucleotides) using cellular mechanisms for the production of polynucleotides. See Weiss et al., Cell. Mol. Life. Sci. 1999, 55:334-358. Others have suggested coupling the oligonucleotide to various moieties to enhance delivery of the oligonucleotide to cells. See Manoharan, M., *Antisense and Nucleic Acid Drug Development.* 2002, 12(2): 103-128

Peptides that specifically home to tumor endothelial cells in various tissues are known. For example, Porkka et al. *Proc. Nat'l Acad. Sci.* (USA) 99: 7444-7449 (2002), which is incorporated herein by reference, describe peptides that home to the nuclei of tumor cells and tumor endothelial cells in vivo. Other cell-type specific homing peptides are described in US Patent Publication Nos. US2003/0152578, US2003/0149235, and US2002/0041898, which are incorporated herein by reference. US Patent Publication No. 2003/0152578 relates to conjugates of these homing peptides with drugs or with detectable labels. US Patent Publication No. 2002/0041898 mentions conjugates of homing peptides with various types of molecules including antisense oligonucleotides, but does not disclose any specific method for this conjugation. U.S. Pat. No. 5,670,617 discloses conjugation of nucleic acids with the HIV tat protein as a transport protein to enhance intracellular delivery.

Harrison et al., *Nucleic Acids Res.* (1998) 26(13): 3136-3145 discloses synthesis of peptide-oligonucleotide conjugates using 4-(maleimidomethyl)-1-cyclohexane carboxylic acid N-hydroxysuccinimde ester (SMCC) as a linker. This paper reports only the use of short peptides, however, to allow assessment of the affect of peptide sequence on antisense activity. These approaches have not provided a general answer to the issue delivery of antisense to cells of interest for efficient reduction of expression of a target protein. When a targeting moiety is added to an oligonucleotide, it may limit the ability of that oligonucleotide to interact with target mRNA for example as a consequence of steric or chemical (hydrophilic/hydrophobic) interactions, alter the ability of the molecule to pass through the cell membrane and/or change the intracellular trafficking pattern for the molecule such that it sequestered in or excreted from the cell, or otherwise made less available for interaction with target nucleotides in the cell.

SUMMARY OF THE INVENTION

The present invention provides therapeutic conjugates for the efficient delivery of sequence-specific antisense to cells of a selected type for the inhibition of a target protein. The therapeutic conjugates of the invention have the general formula:

peptide-HBL-antisense in which the peptide is a homing peptide which directs the conjugate to cells of a particular type, antisense is an antisense oligonucleotide having a sequence selected to provide sequence-specific inhibition of the target protein, and HBL is a heterobifunctional linker having reactivity towards amino and sulfhydryl groups. Exemplary linkers useful as HBL in this formula include SMCC, GMBS (4-maleimidobutyric acid N-hydroxysuccinimide ester) and EMCS ([N-e-Maleimidocaproyloxy]succinimide ester). SMCC, GMBS and EMCS are known linkers that have been used to form conjugates of peptides, for example with larger proteins or polysaccharides, and are commercially available as a cross-linking agent for proteins (www.piercenet.com).

In specific embodiments of the invention, the peptide is a peptide that specifically homes to endothelial cells in the tumor. In preferred embodiments, the peptide portion of the conjugate is the F3 peptide of Seq. ID No. 3.

In specific embodiments, the antisense oligonucleotide that inhibits expression of inhibitor of DNA-binding protein 1 (Id1). In preferred embodiment, the antisense oligonucleotide targeting Id1 has the sequence of SEQ ID Nos. 1 or 2.

The invention further provides a method of using the conjugates of the invention to treat diseases associated with over expression of a target protein. In accordance with this method, a patient, particularly a human patient diagnosed with the disease is treated by administration of a peptide-conjugate antisense oligonucleotide conjugate, in which the peptide portion is selected to direct the conjugate to cells relevant to the disease, and the antisense portion is selected to be a sequence-specific inhibitor of expression of the target protein. In specific embodiments, the method is used to treat cancer, particularly tumors whose growth is very dependent on de novo blood vessel formation.

DETAILED DESCRIPTION OF THE INVENTION

Figure 1:
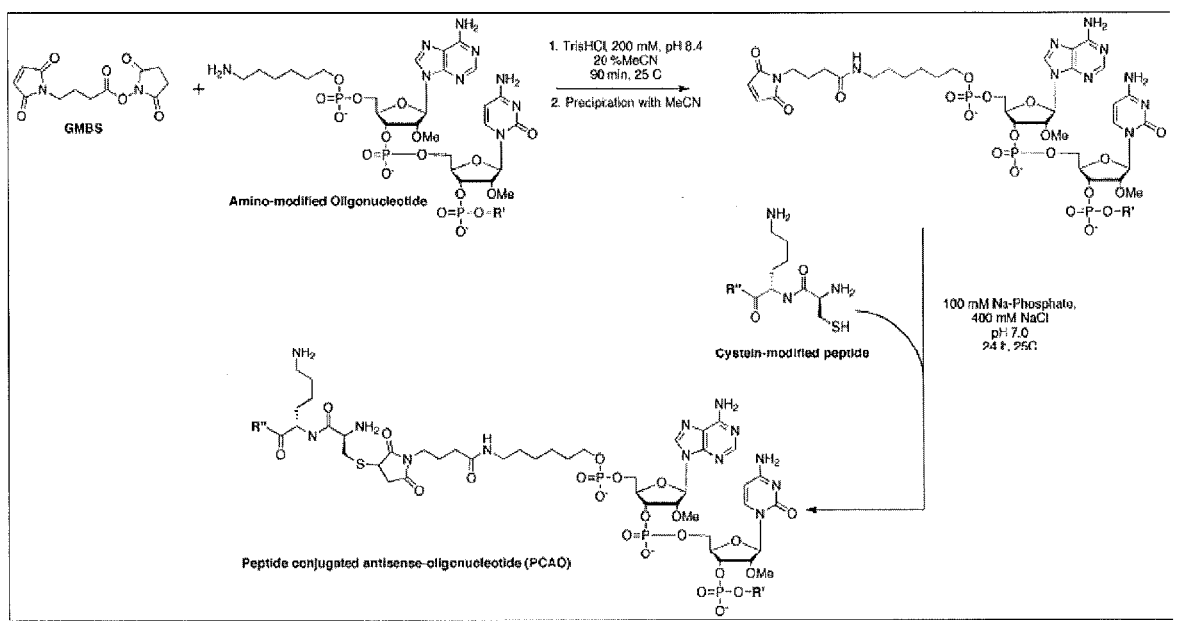
FIG. 1 shows a synthetic procedure for making the peptide conjugated oligonucleotide of the invention.

In the present application the term "peptide-conjugated antisense oligonucleotide" or PCAO refers to a compound of the structure:

peptide-HBL-antisense in which the peptide is a sequence providing cell-type specific targeting. HBL is a heterobifunctional linker and antisense is an antisense oligonucleotide (including DNA, RNA, morpholino oligonucleotides, peptide nucleic acids, LNA or chemically modified derivatives thereof) with sequence-based specificity for a therapeutic target gene found in the targeted cell type. As will be apparent, the peptide and the antisense are selected in compatible pairs, and the general formula should not be construed as covering meaningless combinations of peptides and antisense that would not be expected to have any therapeutic value.

The antisense may be an RNA molecule that forms a double-stranded hairpin (shRNA) or it may be double stranded. In the case where the antisense is part of a double stranded molecule, for example when using siRNA, the peptide may be conjugated with either the sense or the antisense strand, the other strand being associated by hybridization. Thus, in a more general sense, the structure can be described as:

peptide-HBL-sequence-specific oligonucleotide with the sequence specific oligonucleotide portion comprising a sequence-specific antisense oligonucleotide, either as a direct conjugate or via hybridization to a conjugated strand.

Peptides useful in the compounds may be diverse based on the desired target cell-type. The length of the peptide portion is variable, and need only be sufficient to provide the cell-type specificity desired. In some embodiments, the peptide has a length of from 6 to 50 amino acids. Specific peptides include those disclosed in Porkka et al. *Proc. Nat'l Acad. Sci.* (USA) 99: 7444-7449 (2002) and US Patent Publication Nos. US2003/0152578, US2003/0149235, and US2002/0041898. In a specific embodiments of the invention, the peptide portion of compound comprises peptide of the sequence:

(Seq. ID No. 3)
CKDEPQRRSARLSAKPAPPKPEPKPKKAPAKK also referred to herein as HMGN2-F3 or simply F3 which homes to tumor endothelial cells. In other specific embodiments, the peptide portion of the composition is a Grp78 homing peptide such as one comprising the sequence:

sGRP78-1
(Seq. Id No. 4)
WIFPWIQL,
or sGRP78-2
(Seq. ID No. 5)
WDLAWMFRLPVG described in Arap et al. Cancer Cell, 2004, 6(3):275-84 which is incorporated herein by reference. Grp78 homing peptides are useful in targeting the therapeutic agent of the invention to cells for the treatment of glioma. In other specific embodiments, the peptide portion of the compound comprises a tumor endothelial marker as disclosed in St Croix et al. *Science* 289: 119701202 (2000) which is incorporated herein by reference. In still further specific embodiments, the peptide is a tumor endothelial marker as listed in the following table:

| TEM | Accession Number |
| --- | --- |
| Vscp | DQ832275 |
| ETSvg4 (Pea3) | DQ832277 |
| Apelin | DQ832282 | as described in Seaman et al, Cancer Cell, 2007 PMID: 17560335, which is incorporated herein by reference.

In other embodiments, the peptide portion of the composition is a peptide that targets gliomas. Exemplary peptide sequences are:

(Seq. ID No. 33)
TASYSLE (Seq. ID No. 34)
STAASLA (Seq. ID No. 35)
GPFSASP

The oligonucleotide portion of the compound of the invention may likewise be quite variable depending on the specific gene being targeted. In general, it may be any oligonucleotide which has been shown to have sequence specific activity for inhibition of the target gene. In specific embodiments of the invention, the antisense oligonucleotide is targeted to a transcription regulating factor. Examples include antisense targeting inhibitors of DNA bindings (Id1, Id2, Id3 and Id4) which are known for various sources including U.S. Pat. No. 6,372,433, Kleef et al. *Cancer Res.* 1998 Sep. 1; 58(17):3769-72, and Chaudhary et al., *Endocrinology* Vol. 142, No. 5 1727-1736 which are incorporated herein by reference. Other transcription regulating factors include Olig2 (Accession # NP_005797) (Lingon et al, Neuron 2007 PMID: 17296553, Marie et al, Lancet 2001 PMID: 11498220). Antisense to Olig2 with the sequence (5'-TCATCTGCTTCTTGTCCT-3', Seq. Id No. 6) is disclosed in Fu et al., *Development* 129, 681-693 (2002). Still other targets for which antisense oligonucleotides are known include, without limitation bcl-2, BCR-ABL, C-raf-1, Ha-ras, c-myc, PKC, PKA, p53 and MDM2, insulin-dependent growth factor (IGF) and its binding proteins, particularly IGFBP-2 and IGFBP-5. Antisense to kinase suppressor of ras inactivation for therapy of ras mediated tumorigenesis is known from commonly assigned US Patent Publication No. 2006025203 which is incorporated herein by reference. Antisense that specifically hybridizes to a nucleic acid encoding a DNA dependent protein kinase subunit so as to prevent expression of the DNA dependent protein kinase subunit and increase the sensitivity of the cell to heat, chemical, or radiation-induced DNA damage is disclosed in commonly assigned US Patent Publication No. 20050032726 which is incorporated herein by reference.

Sequences useful in siRNA modulation of protein expression are described in numerous sources, including without limitation US Patent Publications 20040077574, 20040127450, 20050042646, 20050124569, 20050137155, 20050171039, 20050196767, 20050209179, 20060094676 which are incorporated herein by reference.

In specific embodiments of the invention, the compound comprises the ID1 targeting antisense sequence gcaccagctccttgaggcgtgag (Seq. ID No. 1) or an RNA counter-part thereof. As used in the specification and claims of this application, the term "RNA counter-part" refers to an RNA molecule in which ribose sugars replace dexoyribose sugars in each base of the sequence and in which T is replaced by U. In preferred embodiments, this sequence is provided as a 5-13-5 gapmer, with the first and last 5 bases in the sequence being 2'-O-methyl RNA bases, and the intervening 13 bases being phosphorothioate linked DNA bases. This preferred oligonucleotide has the sequence: GCACCagctccttgaggcGUGAG (Seq. ID No. 2), with the RNA bases shown in upper case. In other embodiments, the antisense portion has the sequence CAGCCGTTCATGTCGT (Seq. ID No. 31) which targets human-Id1, human-Id3, mouse-Id1, and mouse-Id3, or CAGTGGTTCATGTCGA (Seq ID No. 32) which targets hId3 and mId3.

The peptide portions and the oligonucleotide portions of the compositions of the invention are covalently coupled to one another via the heterobifunctional linker (HBL) that has reactivity with an amino and sulfhydryl groups. In certain embodiments, the heterobifunctional linker is a compound with a maleimide and a succinimide group. The oligonucleotide is connected to the bifunctional linker using the maleimide activity of the linker and an amino functionality on the oligonucleotide. The peptide is reacted with the bifunctional linker via succinimide portion and a sulfhydryl functionality on the peptide.

Known linkers of this type with varying spacers are listed in the following table:

| Name | Spacer properties |
|---|---|
| Maleimidoacetic acid N-hydroxysuccinimide ester | Aryl, C2 |
| 3-Maleimidopropionic acid N-hydroxysuccinimide ester | Aryl, C3 |
| 4-Maleimidobutyric acid N-hydroxysuccinimide ester | Alkyl C4 |
| 6-Maleimidohexanoic acid N-hydroxysuccinimide ester | Alkyl, C6 |
| N-[k-Maleimidoundecanoyloxy]sulfosuccinimide ester | Aryl, C11 |
| 4-(N-Maleimidomethyl)cyclohexanecarboxylic acid N-hydroxysuccinimide ester | Cyclohexyl |
| 3-Maleimidobenzoic acid N-hydroxysuccinimide ester | aryl |
| N-(4-Maleimidophenyl)butyric acid N-hydroxysuccinimide ester | Aryl, alkyl C4 |
| 4-Succinimidyloxycarbonyl-methyl-a-[2-pyridyldithio]toluene | Cleavable, sterically hindered |
| N-Succinimidyl 3-(2-pyridyldithio)-propionate | Short, cleavable |
| Succinimidyl 6-(3-[2-pyridyldithio]-propionamido)hexanoate | Long, cleavable |

Specific examples of compounds within the scope of the present invention include those listed in Table 1.

TABLE 1

| peptide | linker | oligonucleotide |
|---|---|---|
| F3 (Seq. ID No. 3) | GMBS | Seq. ID No. 2 |
| Grp78 targeting (Seq ID No. 4) | GMBS | Seq ID No. 2 |
| F3 (Seq. ID No. 3) | SMCC | Seq. ID No. 2 |
| Grp78 targeting (Seq ID No. 4) | SMCC | Seq ID No. 2 |
| F3 (Seq. ID No. 3) | EMCS | Seq. ID No. 2 |
| Grp78 targeting (Seq ID No. 4) | EMCS | Seq ID No. 2 |
| Grp78 targeting (Seq ID No. 5) | SMCC | Seq. ID No. 2 |
| Grp78 targeting (Seq. ID No. 5) | GMBS | Seq. ID No. 2 |
| Grp78 targeting (Seq ID No. 5) | EMCS | Seq. Id No. 2 |
| Grp78 targeting (Seq ID No. 4) | SMCC | Seq. ID No. 6 |
| Grp78 targeting (Seq. ID No. 4) | GMBS | Seq. ID No. 6 |
| Grp78 targeting (Seq ID No. 4) | EMCS | Seq. Id No. 6 |
| Grp78 targeting (Seq ID No. 5) | SMCC | Seq. ID No. 6 |
| Grp78 targeting (Seq. ID No. 5) | GMBS | Seq. ID No. 6 |
| Grp78 targeting (Seq ID No. 5) | EMCS | Seq. Id No. 6 |

Methods for formation of peptide-oligonucleotide conjugates such as these are known. In particular, the use of a small linker (4-(maleimidomethyl)-1-cyclohexane-carboxylic acid N-hydroxysuccinimide ether, SMCC) for this purpose is described in the Harrison et al., *Nucleic Acids Res.* 26: 3136-3145 (1998), which is incorporated herein by reference, and this method can be used in connection with making the therapeutic agents of the invention. Another specific method which was used to make the compositions described in the examples of this application and which is illustrated in FIG. 1 uses chemistry similar to that of Harris et al., but uses 4-maleimidobutyric acid N-hydroxysuccinimide ester (GMBS) in place of SMCC. GMBS and SMCC have the same reactive groups, the maleimido group and the hydroxysuccinimide group, but differ in the intervening structure or spacer. The same is true of EMCS. Both synthetic methods results in a compound with an HBL, with the oligonucleotide connected directly or indirectly through the nitrogen atom and the peptide connected through a sulfur to a carbon atom of the succinimide ring.

The therapeutic agent of the invention can be administered in various ways, including topically, intra-nasally, and via subcutaneous, retro-orbital, intramuscular, intravenous, and intraperitoneal injection. The amount of the therapeutic agent administered is sufficient to provide a therapeutic affect without inappropriate levels of toxicity. It will be appreciated that the extent of tolerable side effects is dependent on the seriousness of the condition being treated. In general, therapeutic levels of 10%, 25%, 50%, 75% or up to 100% of the maximum tolerated dosage as determined through standard toxicity testing are appropriate.

The therapeutic agent can be formulated in sterile injectable solutions, in lipid carriers, in topical creams and ointments or other carriers dependent on the condition. In addition, in the case of cancer treatments, the therapeutic agent can be formulated or administered with a chemotherapy agent or agents that are effective against the particular cancer. Examples of chemotherapy agents include, without limitation, vinca alkaloids such as vinblastine, navelbine and vindesine; probenicid, nucleotide analogs such as 5-fluorouracil, cytarabine and gemcitabine; alkylating agents such as cyclophosphamide or ifosfamide; cisplatin or carboplatin; leucovorin; taxanes such a paclitaxel or docetaxel; anti-CD20 monoclonal antibodies, with or without radioisotopes, antifolates such as methotrexate, edatrexate and 10-progargyl-10-deazaminopterin; and antibiotics such as doxorubicin and mitomycin.

The therapeutic agents of the invention can, through the appropriate selection of the peptide and the antisense portions of the compound, be used to treat a wide variety of cancers, including without limitation, breast cancer, prostate cancer, lung cancer, glioma and other brain cancers, colorectal cancer, pancreatic cancer, liver cancer, and sarcoma.

Therapeutic Agents with Id1-Targeted Antisense

In one embodiment of the invention, the therapeutic agents of the invention are effective to inhibit expression of Id1, and as a result are useful in the treatment of conditions where angiogenesis is significant, including tumors and diabetic retinopathy. In this embodiment, the homing peptide F3 selectively directs the therapeutic agent to tumor endothelial cells, and as a result helps minimize the side effects of the treatment and elevate local concentration of the active agent (the oligonucleotide).

In order to determine if the Id1 PCAO retained the homing specificity of the F3 peptide and could be taken up by cells in the absence of lipid or other specialized carrier, fluorescence labeled Id1-PCAOs were supplied to different cell lines at a concentration of 200 nM. Confocal fluorescence microscopy showed uptake only by endothelial cells (HUVECs and the murine endothelioma cell line EOMA) whereas all other tested tumor cell lines as well as normal murine embryonic fibroblasts (MEFs) and human dermal fibroblasts (NHDFs) were negative. While the Id1-PCAOs were readily taken up into endothelial cells, no internalization was observed using non-conjugated fluorescence labeled Id1-AOs presumably due to the absence of lipid carrier and the absence of conjugation with the homing peptide. Fluorescein and tetra methyl-rhodamine red labeled PCAOs were also tested to control for the effects of the fluorophore and similar results were obtained. To rule out effects from the fixation process we performed epifluorescence live imaging on viable HUVECs and HeLa cells and similar results were observed. The fluorescent Id1-PCAO derivatives co-localized with nucleolin in the nucleus of HUVECs. This is in accordance with published data suggesting that nucleolin is the cell surface binding partner for F3, and that F3 is transported with nucleolin into the cytoplasm and subsequently into the nucleus.

Homing studies were also performed in animals bearing spontaneous tumors in MMTV-HER2/neu (YD) and PTEN+/− backgrounds. Accumulation of Id1-PCAOs in the tumor endothelium was observed in these models, showing that the homing properties are maintained in spontaneous tumor models. To test if the PCAOs down-regulate Id1 protein levels in vivo, tumor bearing transgenic MMTV-HER2/neu (YD) Id1+/− mice were injected intravenously with Id1-PCAOs. Since repeated application of the drug was necessary to yield significant down-regulation in vitro, the animals were treated with 15 nmol/d of Id1-PCAO or Id1-AO for three consecutive days. Over 80% of tumor vessels in animals treated with Id1-PCAO were completely negative for Id1 expression by IHC. Vessels from animals that received the Id1-AO alone showed no detectable down-regulation of Id1.

Figure 2:
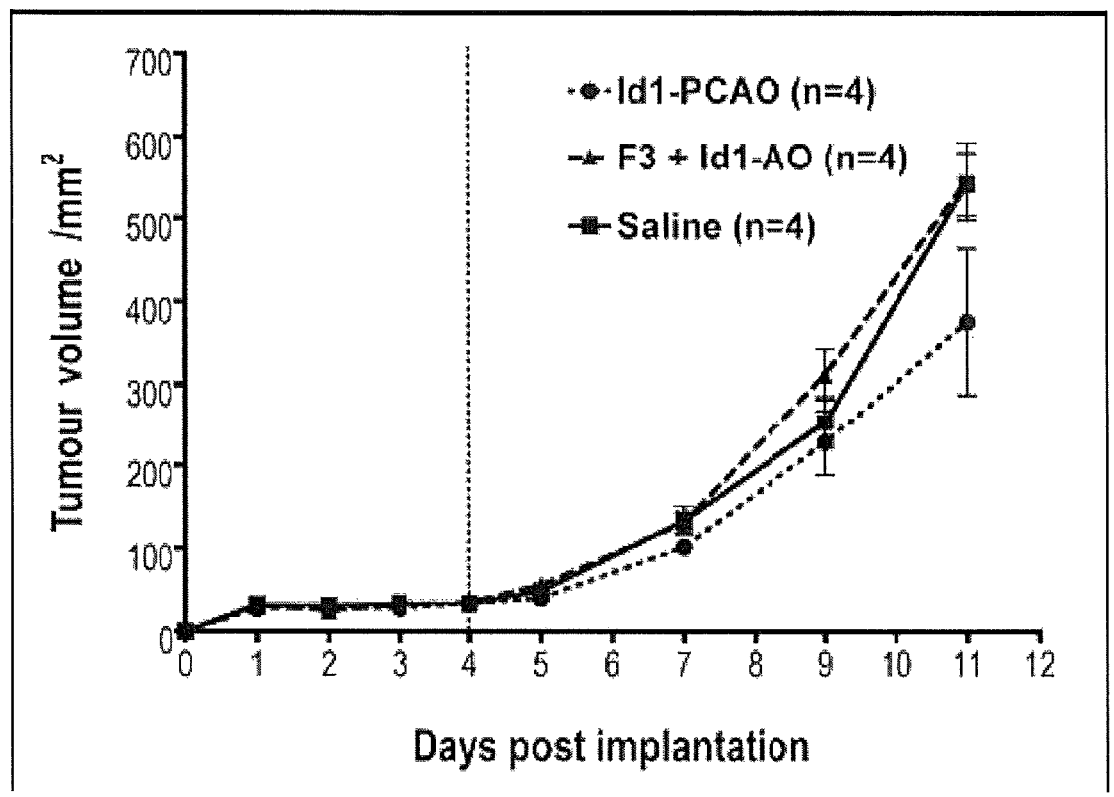
FIG. 2 shows a tumor growth curve for mice treated with 12 nmol/d IV of Id1-PCAO starting on day 4 after tumor implantation (vertical line).
Figure 3:
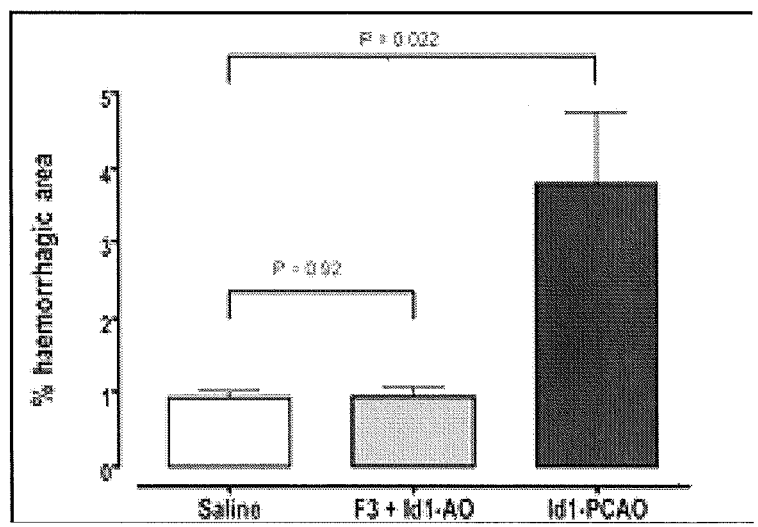
FIG. 3 shows increased haemorrhage in treated tumors.
Figure 4:
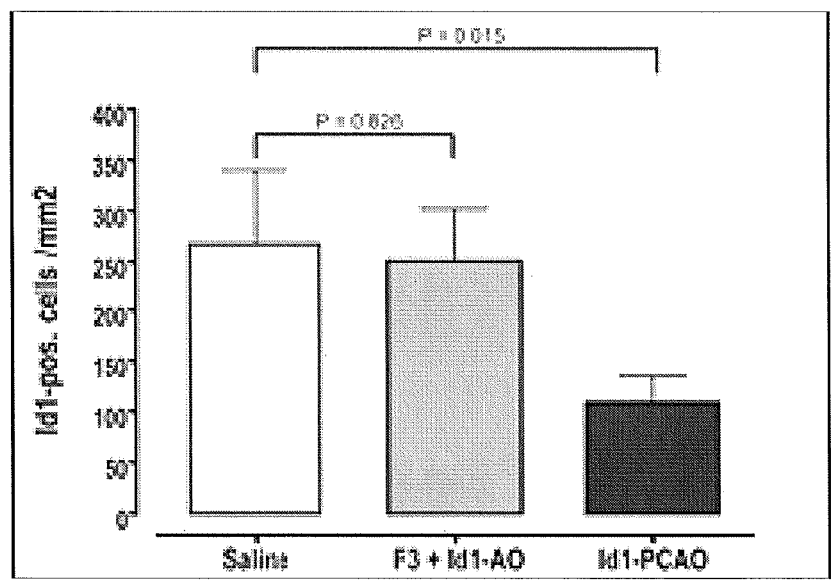
FIG. 4 shows reduction in cells staining positive for Id1 in treated tumors.

The effect of the Id1-PCAOs on a developing allograft tumor was examined. The benefit of this model versus a spontaneous model is that tumor onset and progression time can be controlled. This allows for narrowing of total treatment time as much as possible. Id1 negative cells from a spontaneous tumor formed in a MMTV-HER2/neu (YD) Id−/− animal were employed to ensure that observed effects were caused by Id1 inhibition in the microenvironment, presumably the endothelium, and not the tumor cells. While fluorophore-labeled PCAOs did not accumulate in the tumor cells in short term experiments, we wanted to exclude effects resulting from accumulation of the drug in the tumor when given over a prolonged period. Animals were implanted with MMTVHER2/neu (YD) Id1−/− cells and treated with 10 nmol/d (app. 5.7 mg/kgBW*d, equivalent to 3.7 mg/kg*d pure AO) Id1-PCAO for eight consecutive days by i.v. injection, starting at day 4 when tumors became palpable. Tumor-growth was only modestly, but statistically significantly (P=0.0078) inhibited by treatment with Id1-PCAOs (FIG. 2). Tumor specimens dissected after completion of the treatment however showed a dramatic increase in haemorrhage (FIG. 3, P=0.022, an effect also observed previously in spontaneous tumors arising in Id-deficient mice. Id1-PCAO treated tumors also showed significantly lower counts of Id1-positive endothelial cells, indicating the effectiveness of the drug (FIG. 4, P=0.015 for Id1-PCAO treated versus both, saline and F3+Id1-AO receiving tumors). Id1-PCAOs induced hypoxia as shown by increased staining for Hif1-alpha-expression relative to saline or F3 plus Id1-AO controls. This result was consistent with previously observed analysis of genetic Id1 loss in spontaneous MMTV-HER2/neu (YD) tumors.

Id proteins are attractive targets for anti-angiogenic tumor therapy because (1) they are essential for the mobilization of endothelial progenitors from the bone marrow to the tumor, and (2) are not expressed in normal adult vasculature and lead to severe perturbations in tumor vascular integrity when partially inhibited genetically. However, the hurdles for hitting these targets are significant since Ids are intranuclear proteins which work by direct physical association with other proteins. The results summarized here show that the therapeutic agents of the invention provide the ability to practically realize the potential of the Id proteins (particularly Id1) as targets for use in anti-angiogenic tumor therapy, through the use of the antisense targeting strategy using a homing peptide. The resulting peptide conjugated antisense oligonucleotide (or PCAO) retains its homing specificity and ability to inhibit Id1 protein expression both in vitro and in vivo.

While it has been previously shown that F3 can be used to transport a payload like fluorophores or nanoparticles into the tumor vasculature, it was anticipated that the homing potential of the highly basic F3 peptide might be affected by conjugation to the anionic oligonucleotide. However, surprisingly the PCAO seems to show higher selectivity for endothelial cells than F3 itself which is also taken up by tumor cells in vitro. Furthermore, the tumor vessel phenotype observed after intervention with Id1-PCAOs and after genetic Id1 loss is different than that found after treatment with anti-VEGF agents like the monoclonal antibody Avastin.

Figure 5:
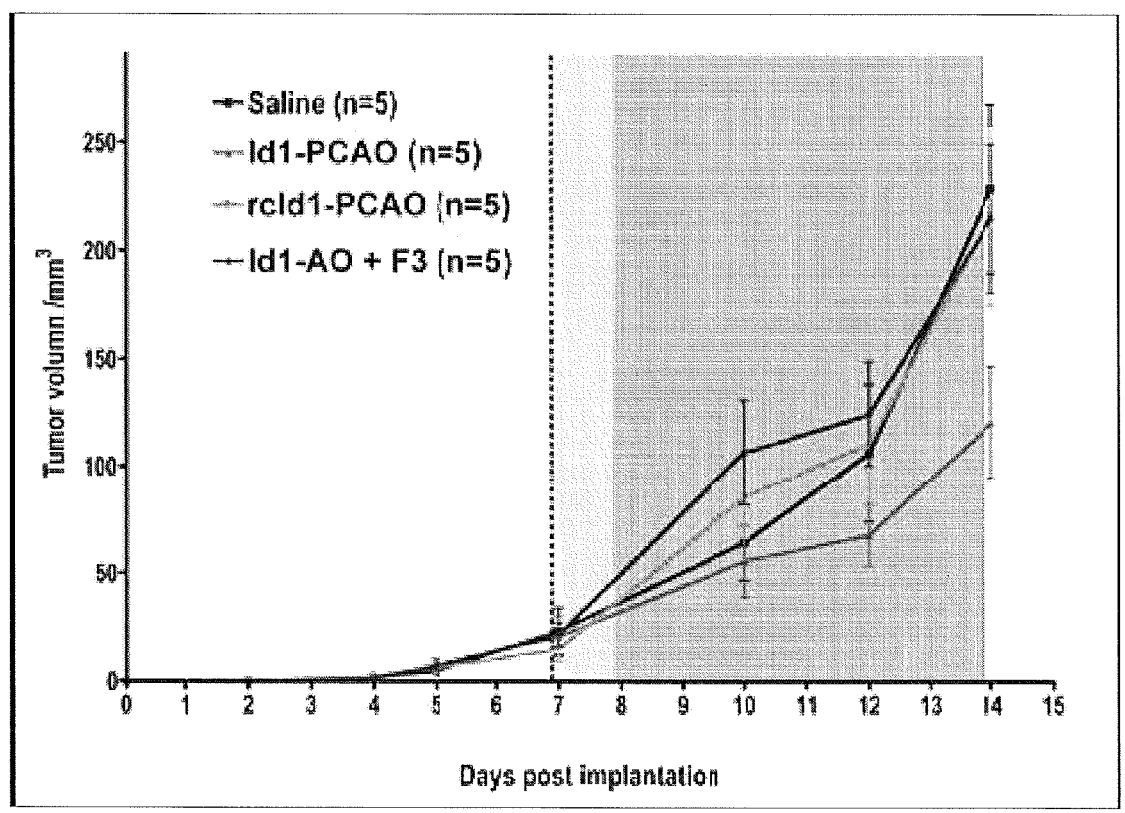
FIG. 5 shows tumor growth in Lewis Lung cell model with various treatments.

In vivo, PCAOs closely recapitulate the effects of Id1 loss observed in genetically manipulated mice which strongly supports the idea that we have effectively hit the intended target. As a single agent Id1-PCAO was able to reduce the growth rate of Lewis Lung cancer (LLC) tumors significantly similar to what has been observed after genetic reduction of Id1 levels. Male C57/B6 were engrafted with GFP/fluc expressing Lewis lung carcinoma cells. After tumor establishment osmotic pumps were implanted to deliver Id1-PCAO or control substances. FIG. 5 shows Tumor growth was followed for 14 days post implantation. Treatment started on day 8 after the pumps implanted on day 7 started working (grey field: working period of pumps during primary tumor growth). As shown, tumor volume was substantially lower with Id1-PCAO treatment (bottom line).

Figure 6:
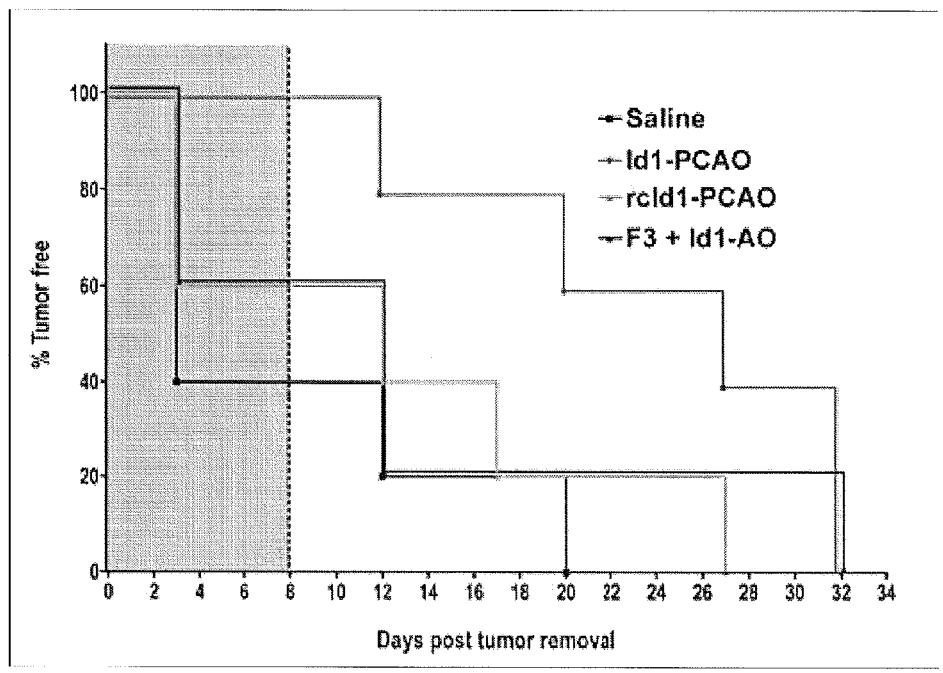
FIG. 6 shows percent of tumor free mice in Lewis Lung cell model after removal of primary tumors with various treatments.

Moreover, after treatment with Id1-PCAOs and removal of primary tumors, metastatic growth of LLC was substantially delayed as was observed after genetic reduction of Id1/3 levels. FIG. 6 shows a Kaplan-Meyer plot of tumor free survival after primary tumors were surgically removed 14 days after injection. Metastatic growth was monitored by intravital bioluminescence imaging (grey field: residual working period of pumps after removal of primary tumors). As shown, the percentage of tumor free mice was substantially greater with the Id1-PCAO treatment (top line).

Increased haemorrhage in treated tumors was also observed in mice treated with Id1-PCAO as compared to the controls.

Importantly, we now have shown that inhibition of Id1 by PCAO in established tumors can also substantially inhibit tumor growth in the LLC model, thus establishing the clinical relevance of the method of the invention. Since we observed increased haemorrhage and vascular permeability in treated tumors which is in general attributed with a higher rate of tumor cell embolization, it is probable that Id1-PCAO interferes with metastasis by blocking angiogenesis in the new distal bed rather than inhibiting escape of cells into the circulation from the primary tumor. Indeed metastatic cells were observed in the lungs of Id1-PCAO treated animals, but these cells failed to colonize as long as treatment was applied. This is in accordance with earlier findings that genetic Id1 loss prevents the establishment of metastasis in the lung after i.v. injection of LLC cells.

In a particularly preferred embodiment, the therapeutic peptide-conjugated oligonucleotide is administered in combination with an inhibitor of Hsp90 such as 17-AAG (17-(allylamino)-17-demethoxygeldanamycin). Other inhibitors of Hsp90 are known, for example from US patent Publications 2004/0102458, 2005/0049263, 2005/0107343, 2005/0113339, 2006/0205705 and 2007/0072855, which are incorporated herein by reference.

Figure 7:
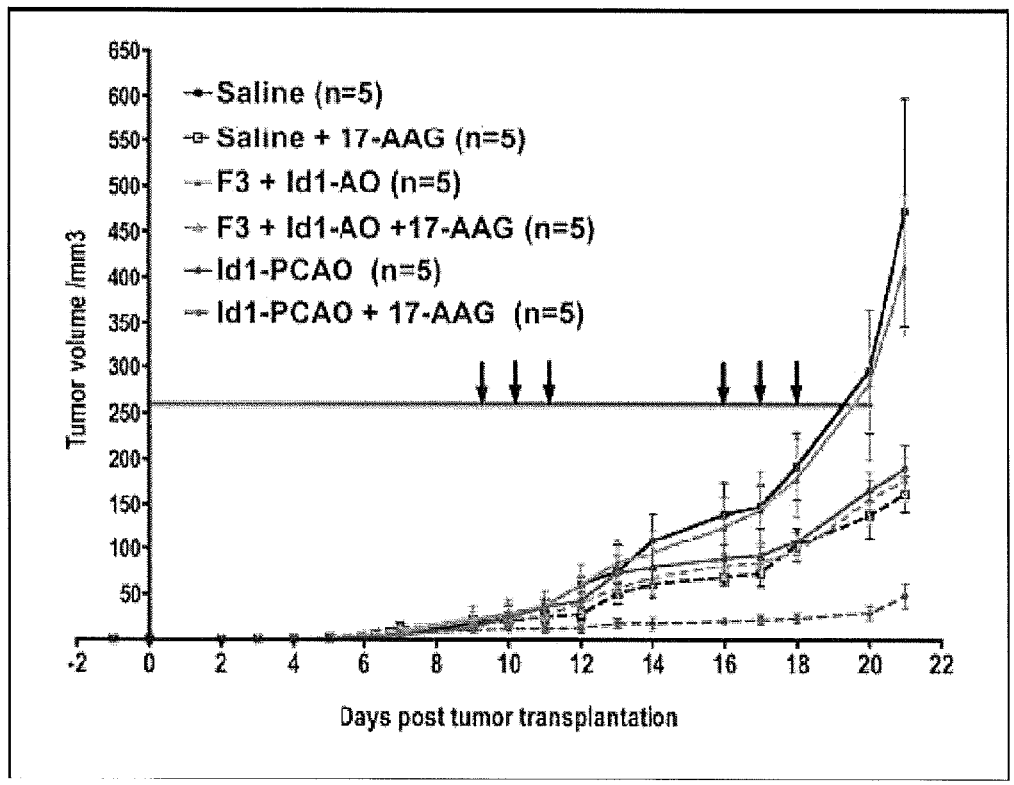
FIG. 7 shows tumor volume following treatment with Id1-PCAO, with and without 17-AAG treatment.

It has been observed previously that genetic Id loss in combination with the Hsp90-inhibitor 17-AAG) was more effective than either alone in reducing tumor burden (de Candia, P. et al. Angiogenesis impairment in Id-deficient mice cooperates with an Hsp90 inhibitor to completely suppress HER2/neu-dependent breast tumors. Proc Natl Acad Sci USA 100, 12337-42 (2003)), perhaps due to the requirement of Hsp90 for maintaining Hif1-alpha or HER2/neu stability. Id1-PCAOs were therefore tested in combination with 17-AAG in the MMTV-HER2/neu (YD) Id1-/- allograft model. The Id1-PCAO was delivered in this prolonged experiment via subcutaneously implanted osmotic pumps (7 nmol/d). 17-AAG was given by intraperitoneal injection according to an established protocol, on 3 consecutive days per week after tumor establishment. As controls, saline or the un-conjugated components of the Id1-PCAO (F3-peptide and Id1-AO each at 20 nmol/d) were administered. Id1-PCAO alone delayed tumor growth to a similar degree as 17-AAG. Combination of both drugs however yielded virtually complete inhibition of tumor growth over the treatment period (FIG. 7, bottom line, P=0.0001, P<0.0001, P=0.0002 versus control, 17-AAG and F3 plus Id1-AO plus 17-AAG respectively). In contrast administration of the antisense oligonucleotide and peptide in un-conjugated form did not inhibit tumor growth and showed no enhancement of the 17-AAG alone effect. To further control for non-specific effects we repeated the experiment using the same tumor model and added this time rcId1-PCAO which was delivered at the same rate as the Id1-PCAO (7 nmol/d) and the F3-peptide without addition of Id1-AO (20 nmol/d) as control substances. In this second experiment Id1-PCAO administration in combination with 17-AAG again had a significant effect on growth (P=0.0079) while neither rcId1-PCAO nor F3 enhanced 17-AAG efficacy (P=0.97 and 1.00 respectively). Injection of Evans blue in selected animals showed massively increased leakage from the Id1-PCAO treated tumor blood vessels likely accounting for the hypoxic stress and sensitivity to 17-AAG. Treatment with Id1-PCAO as well as with 17-AAG alone resulted in a decrease of Id1-positive endothelial cells in the tumor. While Id1-PCAO down-regulated Id1 expression in the cells, 17-AAG lead to a decreased vascular density, which resulted in the lower count for Id1-positive cells. Combination of both drugs further diminished Id1-positive cells. The decrease in Id1-positive cells after administration of Id1-PCAO alone was less dramatic than in the intravenous protocol described above. This might be due to the slight decrease in dosage and the changed route of administration (s.c. vs. i.v.). While Id1-PCAO administration caused up-regulation of Hif1-alpha, 17-AAG injections counteracted this response. The hypoxic regions characteristically surrounded necrotic areas that also displayed signs of cystification.

Adverse effects of Id1-PCAO treatment were not observed. Animals did not suffer from weight loss and wound healing (e.g. after replacement of the subcutaneous implanted pumps) was not grossly impaired. Also, kidneys of all animals were removed after the 3 week treatment and examined and no signs of renal toxicity were observed.

In a further specific example, the therapeutic agent combines a Grp78 targeting peptide with an Id1 targeting antisense oligonucleotide. A therapeutic agent of this type was synthesized using the Grp-78 targeting peptide of Seq. ID No. 4, GMBS as the HBL, and Id1 antisense of Seq. ID No. 2, labeled with FITC and injected retro-orbitally into a mouse model with a high-grade malignant glioma. Four hours post injection the mouse was sacrificed, and tissue was processed for imaging. Grp78-GMBS-ASId1 was observed to accumulate around tumor blood vessels in the imaged tissue, indicating that it crossed the blood brain barrier and selectively accumulated in tumor endothelium.

EXAMPLES

Example 1

Synthesis of F3-ASO Conjugates

Coupling was done according to Harrison and Balasubramanian, Nucleic Acids Res 26, 3136-45 (1998), with some modifications as described below. Fully modified oligonucleotides were obtained directly from Operon Biotechnologies with a C6-amino linker attached to the 5'-end of a gap-mer with the sequence GCACCagctccttgaggcGUGAG (SEQ ID No: 2, upper case: 2'O-methyl RNA bases; lower case phosphorothioate linked DNA bases). The reverse complimentary sequence with the same modification was used as a control oligonucleotide (rcId1-AO and in conjugated form as rcId1-PCAO). For uptake and homing studies, oligos were obtained from the supplier with a 3'-end fluorescein or rhodamine red label. The cysteine modified F3-peptide sequence is CKDEPQRRSARLSAKPAPPKPEPKPKKAPAKK (SEQ ID No: 3).

The oligos were dissolved in 200 mM TrisHCl pH 8.4 to a final concentration of 1 mM and stored at −20° C. 2.8 mg GMBS (4-maleimidobutyric acid N-hydroxysuccinimide ester, 10 μmol, 100 eq.) in 40 μL acetonitrile were added to 100 μL (100 nmol) of the oligo solution. The reaction vessel was wrapped in aluminum foil and incubated with shaking at 25° C. for 90 min. The oligonucleotide was precipitated with 1 mL acetonitril and remaining GMBS was removed by vigorous washing with acetonitril (9×1 mL). After drying in vacuo the activated oligo was dissolved in 50 μL buffer (100 mM Na-phosphate, 400 mM NaCl at pH 7.0) to which 400 nmol F3-N-Cys (4 eq.) in 50 μL buffer (40 mM Na-phosphate, 20 mM EDTA, pH 7.0) were slowly added. The reaction mixture was incubated with shaking for 24 h at 25 C. The coupling-product was purified via reverse phase high performance liquid chromatography (Akta Purifier System, GE Healthcare; Column: OligoDNA RP 150×7.8 mm, Tosoh Bioscience, Montgomeryville, Pa.). To first eluate the non-conjugated peptide a 0.05% TFA in water/acetonitrile gradient (5-20% acetonitrile) was used. To separate the non-conjugated AO from the PCAO a second step was done using an ammonium acetate (20 mM, pH 6.8)/acetonitrile gradient (5-25% acetonitrile). Fractions containing the PCAO were combined, concentrated in a vacuum concentrator system (Eppendorf, Westbury, N.Y.), and precipitated with ethanol. Yields in a multitude of experiments (>10, scales up to 600 nmol) varied between 40 and 78% as calculated from absorbance measurements at 260 nm. Identity of the conjugate was verified by mass spectrometry. Negative ion electrospray ionization mass spectronomy was performed on a Sciex Q-star/Pulsar instrument (MDS Sciex, Concorde, ON). Id1-PCAO: calculated mass: 11441.6 Da, found: 11441.8 Da.

Example 2

Effect of F3-ASO Conjugates on Id1 Expression

HUVEC (4th passage) were seeded 150,000 cells into the wells of six-well dishes (BD Bioscience, San Jose, Calif.). Medium was exchanged after 18 h with standard medium containing either F3-ASO conjugates or ASO at a concentration of 200 nM. The treatment was repeated every 24 h for two more days. Samples were drawn every 24 h by lysis with 150 µL/well M-PER lysis buffer (Pierce). Samples were stored in liquid nitrogen. Protein concentration was determined with the BCA protein assay kit (Pierce), and an equal amount (30 µg) was loaded into the wells of a 4-20% gradient SDS polyacrylamide gel. After electrophoresis the proteins were transferred onto a PVDF membrane and Id1 amounts were detected with an anti-Id1 antibody (C-20, SantaCruz Biotechnology, Santa Cruz, Calif.) and an anti-rabbit-HRP conjugate as secondary antibody (Amersham). Significantly greater reduction in Id1 expression was observed using the F3-Id1-ASO conjugate than using the ASO conjugate alone.

Example 3

Tube Formation Assay

HUVECs (Cambrex, East Rutherford, N.J.) in 4th passage were seeded at 500,000 cells into 25 mL culture flasks in EGM-2 medium. Medium was exchanged after 18 h with standard medium containing either F3-ASO conjugates or ASO at a concentration of 200 nM. The treatment was repeated every 24 h for two more days. 72 h after starting the treatment wells of a 24 well culture dish were covert with 150 µL matrigel and the matrigel was gelatinized for 30 min at 37° C. Pretreated HUVEC were trypsinized, the detached cells were collected by centrifugation and resuspended in EGM-2 media containing the F3-ASO conjugates or ASO at 200 nM. Cells were seeded at 25,000 or 50,000 cells on the gelatinized Matrigel. The plates were incubated at 37° C. with 5% CO2 for 16-18 h. Media was removed, and the matrigel surface was washed twice with 500 µL PBS before cells were labeled with 250 µL 8 µM Calcein AM (Pierce, Rockford, Ill.) in PBS for 30 min at 37° C. After two additional washing steps (500 PBS) cells were visualized under an inverted microscope. Fluorescence was excited at 488 nm and recorded at 538 nm. Well-defined tube formation did not occur in HUVEC treated with F3-Id1-ASO (Id1-PCAO). See Table 2. This shows that treatment with the F3-Id1-ASO conjugate interferes with the ability of HUVEC to form capillary-like structures, which is necessary in angiogenic processes. The tube formation assay is a standard assay for anti-angiogenic drugs as reviewed in Auerbach et al. Clin. Chem. 49 (2003), 32-40.

TABLE 2

| Treatment | Total tube length (mm/mm$^2$) | Branching Points/mm |
|---|---|---|
| Saline | 8.13 ± 0.74 | 270.7 ± 32.18 |
| F3 + ASO | 8.40 ± 0.43 | 322.9 ± 21.09 |
| Id1-PCAO | 3.51 ± 0.66 (P = 0.004) | 116.8 ± 24.88 (P = 0.02) |
| rcId1-PCAO | 8.1 ± 1.05 | 278.2 ± 42.99 |

Example 4

Wound Healing Assay

HUVEC (4th passage) were seeded 100,000 cells into the wells of a fibronectin coated two-well chamber slides (BD Bioscience). Medium was exchanged after 18 h with standard medium containing either F3-ASO conjugates or ASO at a concentration of 200 nM. The treatment was repeated every 24 h for two more days. 72 h after starting the treatment a scratch was applied with a micropipette-tip. Media was removed the cell-layer once washed with PBS and media containing the F3-conjugate or the control ASO was added. The chamber slides were incubated at 37° C. with 5% CO2 for 22 h. The cells were washed with PBS, fixed with 4% paraformaldehyde in PBS for 20 min at r.t., and washed twice with PBS. The slides were mounted and images were taken under a light microscope to access the grade of closure of the applied scratch.

While the applied scratch closed completely in the non-treated and ASO treated cell cultures, a significant inhibition of the wound closing process was observed in the F3-Id1-ASO conjugate treated culture. This indicates that treatment with the F3-Id1-ASO conjugates inhibits the motility of HUVEC. The movement of endothelial cells towards the progressing tumor is an important part of the angiogenic process. Carmeliet P. and Jain R. K., Nature, 407 (2000), 249-257.

Example 5

In Vivo Distribution of F3-Id1-ASO-FITC Conjugates in a PTEN +/− Transgenic Tumor Model 18 nmol of F3-Id1-ASO-FITC conjugate were i.v. injected into a mouse with advanced lymph hyperplasia. After 3 h the animal was sacrificed and organs were removed. The organs were paraformaldehyde-fixed, embedded in OCT-medium and sectioned. Tissue sections were counterstained with Hoechst 33342 and mounted with fluorescence mounting media. Experiments were repeated in the Pten +/− model and twice in YD neu mice.

A strong accumulation of the FITC-signal was observed in the vessel walls of the tumor and in the kidneys. No significant accumulation was observed in other organs (heart, brain, liver, spleen, intestines). The strong signal in the tumor endothelium is consistent with targeted delivery of the active agent (Id1-ASO) by conjugation to F3. The accumulation in the kidneys indicates rapid renal clearance, also observed with other peptide drugs after i.v. application.

Example 6

Down Regulation of Id1 Expression in the Tumor Endothelium of YD Neu Breast Carcinoma YD neu transgenic animals bearing breast carcinoma were treated for 3 subsequent days with 25 nmol of either Id1-ASO or F3-Id1-ASO conjugate in PBS by i.v. injection. 24 h after the last injection animals were sacrificed, the tumor removed, fixed in paraformaldehyde and embedded in parafine. IHC staining was performed for Id1 (antibody C-20, SantaCruz Biotechnology, Santa Cruz, Calif.) on sections. While treatment with antisense alone showed no effect, Id1 expression was no longer observed in the endothelium of F3-Id1-ASO treated tumor.

Example 7

Transfection of Endothelial Cells (ECs) with Antisense Oligonucleotides (AOs)

ECs (HUVEC-2 or MS-1) were seeded 16 h prior to transfection at $10^5$ cells/well in six-well Multi well dishes (MWD) in standard growth media without antibiotics. AOs were re-precipitated with ethanol from sodium acetate (10 mM, ph 4.8) buffer prior to use. Cells were transfected in 1 mL Opti-MEM I media (Invitrogen, Carlsbad, Calif.) with Lipofectin (Invitrogen) or Cytofectin (Gene Therapy Systems, San Diego, Calif.) according to the manufactures' recommendations. The transfection was repeated at 24 and 48 hours.

Example 8

Plasma Stability Assay

Female balb/c mice were bled by submandibular punctuation using a 4.5 mm lancet (Mcdipoint, Mineola, N.Y.). Plasma was separated from heparinized whole blood by centrifugation (18000 g, 5 min at 4° C.). Antisense oligonucleotides and PCAOs were dissolved in plasma at 25 µM and 10 µL aliquots in microfuge tubes and were incubated at 37° C. for the indicated time. After incubation, 5 µL quencher solution (1.6 M NaCl, 100 mM EDTA pH 8.0) were added and the samples were stored at -80° C. For analysis samples were diluted to 60 µL with agarose sample buffer, incubated 5 min at 95° C. and separated in a 1.5% low melting point agarose gel. AOs/PCAOs were visualized with ethidium bromide under UV-light.

Example 9

Transfection of Cells with Id1-PCAOs

HUVEC were seeded 24 h prior to transfection at $10^5$ cells/well in six-well MWDs in standard growth media (EGM-2) without antibiotics. At the day of transfection the AO-conjugates and control oligos were diluted in EGM-2 to the indicated concentration. Media was replaced with the supplemented EGM-2. The procedure was repeated every 24 h for two more days, samples were drawn at the indicated time points and analyzed via western blot. Other cell lines were treated similarly, with the exception that Id1-PCAO was added to standard growth media, DME or RPMI 1640 in accordance to cell type. Uptake studies in different cell lines with fluorescence labeled Id1-PCAO were performed in both the standard growth media (DME, RPMI 1640 or EGM-2) or in OptiMEM I (supplemented with 2% FBS) to control for media effects.

Example 10

Scratch Assay

HUVEC were plated in fibronectin coated two-well chamber slides (BD Bioscience) at $2.5 \times 10^4$ cells/well. Growth media was supplemented with 200 nM Id1-PCAO (or Id1-AO) and renewed every 24 h. 72 h after plating a scratch was applied using a 20 µl pipette tip. Chambers were washed with media and supplemented media was added. 18 h after the scratch was applied, cells were fixed and imaged.

Example 11

Transduction of LLC Cells with an eGFP/Fluc Dual-Modality Reporter

Ecotropic retrovirus based on the SFG vector5, expressing an Aequorea Victoria eGFP/firefly luciferase (eGFP/FLuc) fusion protein was produced in PhoenixE cells and was used with at least $1 \times 10^6$ infectious particles/ml against NIH3T3 cells. The in vitro transduction of early passage LLC cells with the retroviral vector was accomplished by exposing the cell monolayer to a filtered (0.45 µm) culture medium obtained from the vector producer cells for 8 h in the presence of 8 µg/ml polybrene (Sigma, Mo.). Stably transduced cells were enriched by fluorescence assisted cell sorting (FACS) using eGFP-expression as an marker for successful transduction.

Example 12

Proliferation Assay

HUVEC were plated at $2 \times 10^4$ cells in the wells of 24 well MWDs. After 18 h media was exchanged with standard growth media (EGM-2) supplemented with Id1-PCAO or Id1-AO plus F3 (200 nM or 1 mM). Supplemented media was renewed every 24 h. Media was removed from sample plates at different time points, and the plates were stored at -80 C. All samples were analyzed in parallel using the CyQuant system (Invitrogen, Carlsbad, Calif.) according to the manufacture's instructions.

Example 13

Delivery of Id1-PCAOs In Vivo 12 nmol fluorescence-labeled Id1-PCAOs (app 6.8 mg/kg BW) or Id1-AOs were dissolved in TBS and injected into the tail vein or subcutaneously of tumor-bearing mice. Mice were sacrificed, organs and tumors were dissected, fixed overnight in 4% PFA and finally immersed in 20% sucrose for 24 h. After embedding in OCT (Miles Inc., Elkhart, Ind.) and sectioning, samples were probed for CD31 using a biotinylated secondary antibody and a streptavidin-Alexa488 conjugate as a tertiary agent.

Example 14

Allograft Model of Her2-Overexpressing Breast Cancer

Female nude NCR mice (Taconic) were engrafted with $5 \times 10^6$ MMTV-HER2/neu (YD) Id1-/- tumor cells in the left flank. The animals were randomly divided to three cohorts of four animals and treatment was started 96 h later when tumors became palpable. The first cohort received 10 nmol Id1-PCAO conjugate in 200 µL TBS. The other two cohorts served as negative controls and received either TBS or 10 nmol F3-peptide plus 10 nmol Id1-AO in TBS (app. 5.7 mg/kg BW). Application of the conjugate and control solutions was performed by intravenous injection into the tail vein and was repeated every 24 h for 7 consecutive days. 24 h after the last injection animals were sacrificed. Tumors, kidneys, livers and femurs were collected, fixed with paraformaldehyde, and embedded in paraffin.

Alternatively, animals were implanted s.c. with osmotic pumps (Durect Corp., Cupertino, Calif.) that delivered 7 nmol/d Id1-PCAO (3.5 mg/kg BW) in TBS over a 14 day period. Controls received 20 nmol/d F3-peptide plus 20 nmol/d Id1-AO (in TBS) or TBS. 2×106 MMTV-HER2/neu (YD) Id1−/− tumor cells were injected into the left flank 24 h after implantation of the pumps. After the 14 days treatment period, pumps were replaced using a model with a work period of 7 days. Treatment with 17-AAG (75 mg/kg, i.p. on 3 consecutive days/week) was started when tumors reached a size of 20 mm3. 17-AAG was dissolved at 50 mg/kg in DMSO and diluted with EPL 1:1 before injection. Control animals received DMSO:EPL 1:1 i.p at the same schedule. Tumor size was measured using a calliper. Volume was calculated as V=(/6×longest diameter×perpendicular diameter2).

Example 15

Allograft Model of Metastatic Lewis Lung Carcinoma (LLC)

7.5×10$^5$ Dual reporter labeled LLC cells were implanted in the right dorsal flank of male C57J/B6 mice (Jackson laboratories, Bar Harbour). After seven days, animals were implanted with osmotic pumps (100 µL volume, work period 14 days). The pumps were filled with saline solution of either Id1-PCAO (3.5 mM), rcId1-PCAO (3.5 mM) or F3-peptide plus Id1-AO (12.5 mM each). Concentration and release rate of the pumps resulted in a delivery rate of 229 µg/d (Id1-PCAO and rcId1PCAO) or 265 µg/d and 580 µg (F3 and Id1-AO). 14 days after tumor implantation animals were anaesthetised and primary tumors were surgically removed. Complete removal of the tumor tissue was checked 3 days post operation by in vivo luciferase imaging and re-growing primary tumors were removed. For in vivo luciferase imaging, 100 µL of D-luciferin (Gold Bio Technology, St. Louis, Mo.; 15 mg/mL potassium-salt in PBS) were injected retro-orbitally to animals anaesthetised by isofluorane inhalation. Photographic and luminescence images were acquired using an IVIS 100 system (Xenogen, Hopkinton, Mass.). Animals were sacrificed when distressed. Tumor burden and metastasis data acquired by in vivo luminescence was confirmed by histology.

Image acquisition and analysis: Epifluorescence, bright field and phase contrast images were acquired using Zeiss Axiostar 200 microscopes. Leica laser confocal microscopes were used for co-localisation studies. For quantification, large fields of the tissue sections were acquired using an automated image acquisition and montaging system (Zeiss Axiostar 200M microscope with MetaMorph Software, Molecular Devices, Sunnyvale, Calif.). For evaluation of single cell staining (Id1, CD31, Hif1-alpha) an average of 30 adjacent, single images were acquired from the centre of the section using a 20× objective. Images were montaged to yield one large image covering an average area of 0.82 mm2. Three or 4 large field images were used to quantify each section. Stained areas were quantified using MetaMorph or ImageJ software (http://rsb.info.nih.gov/ij/). Images were thresholded and stained area (CD31) was calculated or particles per field were counted (Id1 or Hif1 positive cells). To quantify extent of haemorrhage, H&E whole tumor sections were imaged with a 5× objective and evaluated using the colour threshold function of the Metamorph software.

Example 16

Targeting of Murine Mammary Carcinoma

A conjugate was prepared using peptide sGRP78 (CWIFPWIQL, Seq ID No. 7), a peptide that binds to GRP78, a stress response chaperone expressed on the surface of various tumors was tested for its ability to transport oligonucleotides into tumor cells. The peptide was conjugated to an anti-Id1 oligonucleotide using GMBS via a 5'-amino linker. The oligonucleotide was labeled with fluorescein at the 3'-end. Accumulation of the oligonucleotide was monitored via the fluorescent label, and was found to occur in 4T1 murine mammary carcinoma cells in mice. Accumulation was also seen in kidney cells, but not in lever or heart. Accumulation was not seen in the carcinoma when the peptide portion of the conjugate was omitted.

Example 17

Accumulation Using Different Homing Peptide

Quantification of tumor-uptake was performed with 111-Indium labeled PCAOs containing Id1 antisense coupled to the peptide via a GMBS linker. Four different peptides were modified with a DOTA (1,4,7,10-tetraazacyclododecane-1,4,7,10-tetraacetic acid) chelator at the N-terminus during standard solid phase peptide synthesis. After conjugation to the antisense oligonucleotide the DOTA group was used to attach an $^{111}$In-ion. The labeled PCAOs were injected into 4T1-breast carcinoma bearing animals, and tumor accumulation was measured after 2 h by resecting the tumor and quantifying gamma-radiation emitted from the sample.

Figure 8:
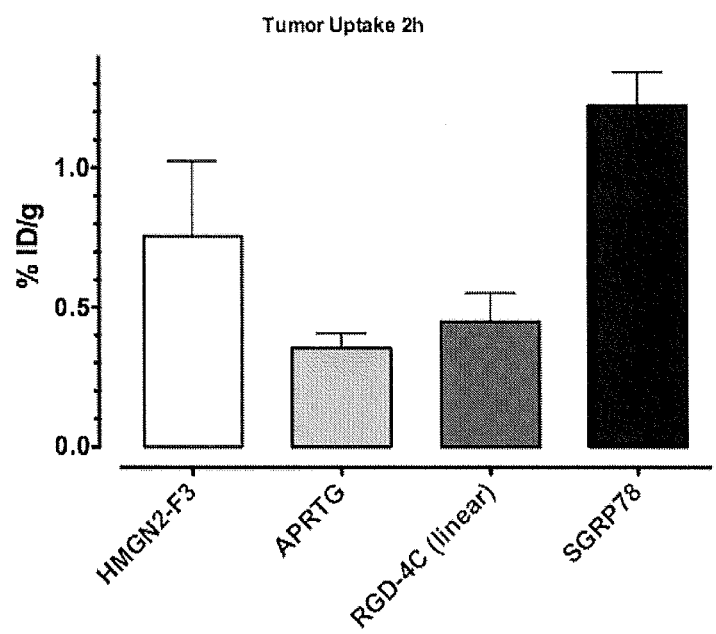
FIG. 8 shows accumulation of conjugates in 4T1 breast carcinoma using different peptide portions.

The peptides used were HMGN2 (Seq. ID No. 3), CAPRPG (Oku et al., Oncogene, 2004, Seq. ID No. 8), RGD-4C (ACDCRGDCFCG, Seq. ID No. 9) and CWIFPWIQL (Seq. ID No. 7). The results are summarized in FIG. 8. As shown, all four peptides resulted in accumulation of $^{111}$In-labeled conjugates in 4T1 beast carcinomas, although to differing extents.

Example 18

Additional Homing Sequences

To identify peptide sequences displaying homing potential to specific tumors or to the vasculature of specific tumors, in vivo phage display panning was performed. Utilizing commercially available M13-based phage libraries (PhD-7 Prod# E8100S and PhD-C7C E8120S, New England Biolabs, Ipswich, Mass.) phage were isolated that were enriched after 3-4 rounds of panning in different tumor models. These phage particles display surface peptides that potentially confer homing and cellular uptake capabilities.

Angiosarcoma Model

Panning was conducted in SVR (ATCC CRL-2280, a murine endothelial cell line) tumor allograft bearing mice. Tumors were resected 24 h post phage injection.

Enriched Sequences:

| Sequence ID | Sequence | Frequency |
|---|---|---|
| 10 | FPGGYTP | 11/15 |
| 11 | MFEPVLP | 1/15 |
| 12 | TLSKQST | 1/15 |
| 13 | TSLKMQV | 1/15 |
| 14 | ERVLMQV | 1/15 |

Breast Carcinoma Model, Tumor Cell Homing Phage

Panning was conducted in 4T1 (ATCC CRL-2539) tumor allograft bearing mice. Tumors were resected 24 h post phage injection.

Enriched Sequences:

| Sequence ID | Sequence | Frequency |
|---|---|---|
| 15 | KWGSNNL | 4/12 |
| 16 | YSMPAPV | 2/12 |
| 17 | DSTRPHY | 2/12 |
| 18 | KYESAPT | 1/12 |
| 19 | TSMTSYR | 1/12 |
| 20 | EKNLTRP | 1/12 |
| 21 | HTPMALE | 1/12 |

Breast Carcinoma Model, Tumor Vascular Homing Phage

Panning was conducted in 4T1 (ATCC CRL-2539) tumor allograft bearing mice. Tumors were resected 5-7 h post phage injection.

Enriched Sequences:

| Sequence ID | Sequence | Frequency |
|---|---|---|
| 22 | GHSKAMY | 4/12 |
| 23 | GHGASIS | 1/12 |
| 24 | NLLAPAG | 1/12 |
| 25 | HDLPAVR | 1/12 |
| 26 | AMPLPVP | 1/12 |
| 27 | HESTWGP | 1/12 |
| 28 | CDPRNPNWC | 1/12 |
| 29 | CLPRHDPYC | 1/12 |
| 30 | CPAGQNAHC | 1/12 |

Seq ID Nos. 10-30 can be used in conjugates in accordance with the present invention.

Example 19

Determination of Glioma Targeting Peptides

Using Nestin-tva mice on an Arf−/− background, glioma formation was induced through stereotaxic injection of DF-1 infected RCAS-PDGFB cells into the adult subventricular zone (SVZ). These mice developed high-grade gliomas, including glioblastomas, demonstrating similar histopathology to human tumors including microvascular proliferation and pseudopalisading necrosis.

Using this mouse model, in vivo panning was carried out with random heptapeptide phage-display libraries. Tumor bearing mice were injected retro-orbitally with $2.0\times10^{11}$ linear and $2.0\times10^{11}$ circular random heptapeptide phage display libraries from New England Biolabs (catalog items Ph.D.-C7C and Ph.D.-7). 24 hours later, mice were sacrificed and tumors were isolated and dissociated using standard papain digestion methods. Cells were then stripped (to select for internalized phage) and lysed. Phage was amplified and purified according to manufacturer instructions. Purified phage ($2.0\times10^{11}$) was then re-injected back into tumor bearing mice and the process was repeated for a total of 5 rounds of in vivo panning. At the end of the 5th round, prior to amplification, phage particles were plated out and individual colonies were selected for sequencing. Those sequences that were enriched (ie—sequences that come up multiple times) were selected for further analysis.

After 5 rounds of panning, three peptide sequences were found that are enriched in gliomas. These sequences are:

```
                        (Seq. ID No. 33)
TASYSLE (Seq. ID No. 34)
STAASLA (Seq. ID No. 35)
GPFSASP
```

All references cited herein are hereby incorporated by reference.

To Applicant's knowledge, the present invention is the first successful targeted, in vivo delivery of an antisense molecule with demonstrated preclinical efficacy. While antisense and targeting peptides have been described before, they have never been fused in a way that allows both moieties to maintain their activities. Thus, the present invention provides the following substantial advances over the art.

The invention claimed is:

1. A method of treating a cancer in an individual in need of treatment for the cancer comprising administering to the individual a therapeutically effective amount of a peptide-oligonucleotide conjugate having the general formula:

homing element-GMBS-antisense in which homing element is a means for directing the conjugate to cells of the cancer, antisense is an antisense gapmer oligonucleotide having a sequence selected to provide sequence-specific inhibition of a target protein, and GMBS is a linking group formed by reaction of 4-maleimidobutyric acid N-hydroxysuccinimide ester with the homing element and the antisense.

2. The method of claim 1, further comprising the step of administering an inhibitor of hsp90.

3. The method of claim 1, wherein the cancer is selected from the group consisting of breast cancer, prostate cancer, lung cancer, glioma and other brain cancers, colorectal cancer, pancreatic cancer, liver cancer, and sarcoma.

4. The method of claim 1, wherein the antisense gapmer oligonucleotide targets a transcription regulating factor in a sequence specific manner.

5. The method of claim 1, wherein the antisense gapmer oligonucleotide targets Id1.

6. The method of claim 5, wherein the antisense gapmer oligonucleotide comprises the sequence gcaccagctccttgag-gcgtgag (Seq. ID No. 1) or an RNA counter-part thereof.

7. The method of claim 1, wherein the homing element directs the conjugate to tumor endothelium.

8. The method of claim 7, wherein the homing element portion of the conjugate comprises a peptide of the sequence:

(Seq. ID No. 3)
CKDEPQRRSARLSAKPAPPKPEPKPKKAPAKK.

9. The method of claim 7, wherein the homing element portion of the conjugate comprises a peptide of the sequence:

(Seq. ID No. 4)
WIFPWIQL
or
(Seq. ID No. 5)
WDLAWMFRLPVG.

10. The method of claim 7, wherein the antisense gapmer oligonucleotide targets a transcription regulating factor in a sequence specific manner.

11. The method of claim 7, wherein the antisense gapmer oligonucleotide targets Id1.

12. The method of claim 11, wherein the antisense gapmer oligonucleotide comprises the sequence gcaccagctccttgag-gcgtgag (Seq. ID No. 1) or an RNA counter-part thereof.

13. The method of claim 1, wherein the homing element portion of the conjugate comprises a sequence selected from Seq. ID Nos. 10-30 and 33-35.

14. The method of claim 1, wherein the antisense gapmer oligonucleotide consists of SEQ ID NO.: 2.

15. The method of claim 1, wherein the cancer is glioma and the means for directing the conjugate to cells of a particular type targets the conjugate to glioma cells.

16. The method of claim 15, wherein the homing element portion of the conjugate comprises a sequence selected from the group consisting of SEQ ID NOs: 33, 34 and 35.

17. The method of claim 1, wherein the cancer is a sarcoma, and the means for directing the conjugate to cells of a particular type targets the conjugate to angiosarcoma cells.

18. The method of claim 17, wherein the homing element portion of the conjugate comprises a sequence selected from the group consisting of SEQ ID NOs: 10, 11, 12, 13, and 14.

19. The method of claim 1, wherein the cancer is breast cancer and the means for directing the conjugate to cells of a particular type targets the conjugate to breast cancer cells.

20. The method of claim 19, wherein the homing element portion of the conjugate comprises a sequence selected from the group consisting of SEQ ID NOs: 15, 16, 17, 18, 19, 20, 21, 22, 23, 24, 25, 26, 27, 28, 29 and 30.

21. A method of treating a cancer in an individual in need of treatment for the cancer comprising administering to the individual a therapeutically effective amount of a peptide-oligonucleotide conjugate having the general formula:

peptide-HBL-antisense in which peptide is a homing peptide which directs the conjugate to cells of the cancer, antisense is an antisense oligonucleotide having a sequence selected to provide sequence-specific inhibition of a target protein, and HBL is a heterobifunctional linker having reactivity towards amino and sulfhydryl groups, and in which the antisense oligonucleotide comprises the Seq ID No. 1 or 31 or an RNA counter-part thereof.

22. The method of claim 21, wherein the peptide directs the conjugate to tumor endothelium.

23. The method of claim 21, wherein HBL is GMBS or EMCS.

* * * * *

SEQUENCE LISTING

<160> NUMBER OF SEQ ID NOS: 35

<210> SEQ ID NO 1
<211> LENGTH: 23
<212> TYPE: DNA
<213> ORGANISM: Homo sapiens

-continued

<400> SEQUENCE: 1
gcaccagctc cttgaggcgt gag                                              23

<210> SEQ ID NO 2
<211> LENGTH: 23
<212> TYPE: DNA
<213> ORGANISM: Artificial Sequence
<220> FEATURE:
<223> OTHER INFORMATION: antisense oligonucleotide targeting ID1.

<400> SEQUENCE: 2
gcaccagctc cttgaggcgu gag                                              23

<210> SEQ ID NO 3
<211> LENGTH: 32
<212> TYPE: PRT
<213> ORGANISM: Artificial Sequence
<220> FEATURE:
<223> OTHER INFORMATION: HMGN2-F3 homing peptide for tumor endothelium

<400> SEQUENCE: 3

Cys Lys Asp Glu Pro Gln Arg Arg Ser Ala Arg Leu Ser Ala Lys Pro
1               5                   10                  15

Ala Pro Pro Lys Pro Glu Pro Lys Pro Lys Ala Pro Ala Lys Lys
            20                  25                  30

<210> SEQ ID NO 4
<211> LENGTH: 8
<212> TYPE: PRT
<213> ORGANISM: Artificial Sequence
<220> FEATURE:
<223> OTHER INFORMATION: GRP78 homing peptide

<400> SEQUENCE: 4

Trp Ile Phe Pro Trp Ile Gln Leu
1               5

<210> SEQ ID NO 5
<211> LENGTH: 12
<212> TYPE: PRT
<213> ORGANISM: Artificial Sequence
<220> FEATURE:
<223> OTHER INFORMATION: GRP78 homing peptide

<400> SEQUENCE: 5

Trp Asp Leu Ala Trp Met Phe Arg Leu Pro Val Gly
1               5                   10

<210> SEQ ID NO 6
<211> LENGTH: 18
<212> TYPE: DNA
<213> ORGANISM: Artificial Sequence
<220> FEATURE:
<223> OTHER INFORMATION: antisense to Olig2

<400> SEQUENCE: 6
tcatctgctt cttgtcct                                                    18

<210> SEQ ID NO 7
<211> LENGTH: 9
<212> TYPE: PRT
<213> ORGANISM: Artificial Sequence
<220> FEATURE:
<223> OTHER INFORMATION: peptide sGRP78

<400> SEQUENCE: 7

```
Cys Trp Ile Phe Pro Trp Ile Gln Leu
1               5

<210> SEQ ID NO 8
<211> LENGTH: 6
<212> TYPE: PRT
<213> ORGANISM: Artificial Sequence
<220> FEATURE:
<223> OTHER INFORMATION: APRTG

<400> SEQUENCE: 8

Cys Ala Pro Arg Pro Gly
1               5

<210> SEQ ID NO 9
<211> LENGTH: 11
<212> TYPE: PRT
<213> ORGANISM: Artificial Sequence
<220> FEATURE:
<223> OTHER INFORMATION: RGD-4C

<400> SEQUENCE: 9

Ala Cys Asp Cys Arg Gly Asp Cys Phe Cys Gly
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Angiosarcoma homing probe

<400> SEQUENCE: 10

Phe Pro Gly Gly Tyr Thr Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Angiosarcoma homing probe

<400> SEQUENCE: 11

Met Phe Glu Pro Val Leu Pro
1               5

<210> SEQ ID NO 12
<211> LENGTH: 7
<212> TYPE: PRT
<213> ORGANISM: Artificial Sequence
<220> FEATURE:
<223> OTHER INFORMATION: Angiosarcoma homing probe

<400> SEQUENCE: 12

Thr Leu Ser Lys Gln Ser Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Angiosarcoma homing probe

<400> SEQUENCE: 13
```

Thr Ser Leu Lys Met Gln Val
1               5

<210> SEQ ID NO 14
<211> LENGTH: 7
<212> TYPE: PRT
<213> ORGANISM: Artificial Sequence
<220> FEATURE:
<223> OTHER INFORMATION: Angiosarcoma homing probe

<400> SEQUENCE: 14

Glu Arg Val Leu Met Gln Val
1               5

<210> SEQ ID NO 15
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 15

Lys Trp Gly Ser Asn Asn Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 16

Tyr Ser Met Pro Ala Pro Val
1               5

<210> SEQ ID NO 17
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 17

Asp Ser Thr Arg Pro His Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 18

Lys Tyr Glu Ser Ala Pro Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 19

Thr Ser Met Thr Ser Tyr Arg

```
1               5

<210> SEQ ID NO 20
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 20

Glu Lys Asn Leu Thr Arg Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Breast Carcinoma homing probe

<400> SEQUENCE: 21

His Thr Pro Met Ala Leu Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 22

Gly His Ser Lys Ala Met Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 23

Gly His Gly Ala Ser Ile Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 24

Asn Leu Leu Ala Pro Ala Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 25

His Asp Leu Pro Ala Val Arg
1               5
```

```
<210> SEQ ID NO 26
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 26

Ala Met Pro Leu Pro Val Pro
1               5

<210> SEQ ID NO 27
<211> LENGTH: 7
<212> TYPE: PRT
<213> ORGANISM: Artificial Sequence
<220> FEATURE:
<223> OTHER INFORMATION: Breast carcinoma  tumor vascular homing probe

<400> SEQUENCE: 27

His Glu Ser Thr Trp Gly Pro
1               5

<210> SEQ ID NO 28
<211> LENGTH: 9
<212> TYPE: PRT
<213> ORGANISM: Artificial Sequence
<220> FEATURE:
<223> OTHER INFORMATION: Breast carcinoma  tumor vascular homing probe

<400> SEQUENCE: 28

Cys Asp Pro Arg Asn Pro Asn Trp Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Breast carcinoma  tumor vascular homing probe

<400> SEQUENCE: 29

Cys Leu Pro Arg His Asp Pro Tyr Cys
1               5

<210> SEQ ID NO 30
<211> LENGTH: 9
<212> TYPE: PRT
<213> ORGANISM: Artificial Sequence
<220> FEATURE:
<223> OTHER INFORMATION: Breast carcinoma  tumor vascular homing probe

<400> SEQUENCE: 30

Cys Pro Ala Gly Gln Asn Ala His Cys
1               5

<210> SEQ ID NO 31
<211> LENGTH: 16
<212> TYPE: DNA
<213> ORGANISM: Artificial Sequence
<220> FEATURE:
<223> OTHER INFORMATION: antisense targeting human or murine ID1 and ID3.

<400> SEQUENCE: 31
cagccgttca tgtcgt                                                       16
```

```
<210> SEQ ID NO 32
<211> LENGTH: 16
<212> TYPE: DNA
<213> ORGANISM: Artificial Sequence
<220> FEATURE:
<223> OTHER INFORMATION: antisense targeting human or murine Id3.

<400> SEQUENCE: 32
cagtggttca tgtcga                                                       16

<210> SEQ ID NO 33
<211> LENGTH: 7
<212> TYPE: PRT
<213> ORGANISM: murine

<400> SEQUENCE: 33

Thr Ala Ser Tyr Ser Leu Glu
1               5

<210> SEQ ID NO 34
<211> LENGTH: 7
<212> TYPE: PRT
<213> ORGANISM: murine

<400> SEQUENCE: 34

Ser Thr Ala Ala Ser Leu Ala
1               5

<210> SEQ ID NO 35
<211> LENGTH: 7
<212> TYPE: PRT
<213> ORGANISM: murine

<400> SEQUENCE: 35

Gly Pro Phe Ser Ala Ser Pro
1               5
```